United States Patent [19]

Elgas

[11] Patent Number: 5,101,671
[45] Date of Patent: Apr. 7, 1992

[54] COMPRESSED GAS SAMPLING DEVICE

[76] Inventor: David H. Elgas, 4886 Cannington Dr., San Diego, Calif. 92117

[21] Appl. No.: 591,677

[22] Filed: Oct. 1, 1990

[51] Int. Cl.⁵ ............................................. G01N 1/22
[52] U.S. Cl. ............................... 73/863.23; 73/863.57
[58] Field of Search ........... 73/863.23, 863.24, 863.25, 73/863.57, 863.86, 864

[56] References Cited

U.S. PATENT DOCUMENTS

| | | | |
|---|---|---|---|
| 3,186,234 | 6/1965 | Solnick et al. | 73/863.71 |
| 3,372,274 | 3/1968 | Landolt | 73/863.23 X |
| 4,576,054 | 3/1986 | Lalin | 73/863.03 |
| 4,689,052 | 8/1987 | Ogren et al. | 55/17 |
| 4,738,147 | 4/1988 | Tomlin | 73/864.81 |
| 4,800,761 | 1/1989 | Spencer | 73/863.71 |
| 4,856,352 | 8/1989 | Daum et al. | 73/863.23 X |
| 4,979,403 | 12/1990 | Pike | 73/863.23 X |

*Primary Examiner*—Tom Noland
*Attorney, Agent, or Firm*—Calif K. Tervo

[57] ABSTRACT

A sampling device for sampling the output of compressed gas sources, such as air compressors, for solid contaminants, such as debris and oil mist, and for gaseous contaminants, such as carbon monoxide and for obtaining filter samples and plenum samples for laboratory analysis generally comprises a manifold including a first conduit and a second conduit, a filter device, a safety valve, a sampling bomb, a flow director valve, and a pressure control valve. The first conduit has a gas receiving end and a filter device end. The second conduit has an inlet end connected to the first conduit and a vent end. A flow director valve at the junction of the first and second conduits is operable from a full shunt position wherein all incoming gas is directed into the second conduit and a full open position wherein incoming gas is directed to the filter or the second conduit. A pressure control valve disposed in the second conduit near the vent end controls the exit of gas out the vent. A sampling bomb is connected to the second conduit between the inlet end and the pressure control valve. A pressure relief valve may also be so connected. This sampling device enables a user to sample with a single device compressors of widely varying pressure and volume outputs while the compressor is operating at its maximum output.

18 Claims, 1 Drawing Sheet

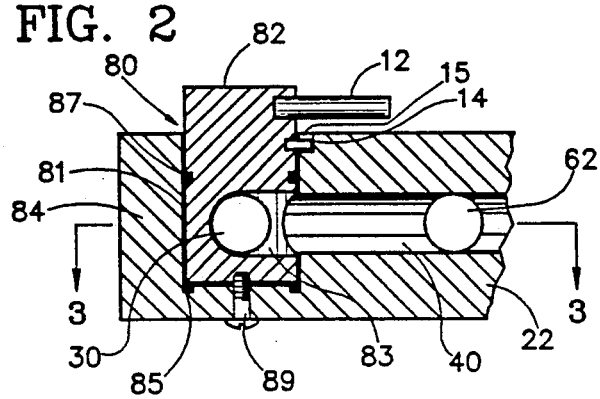
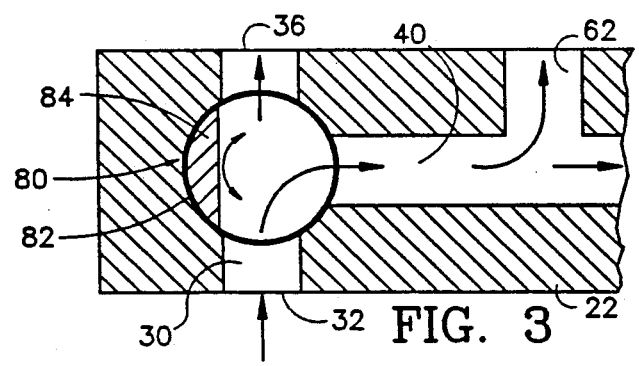
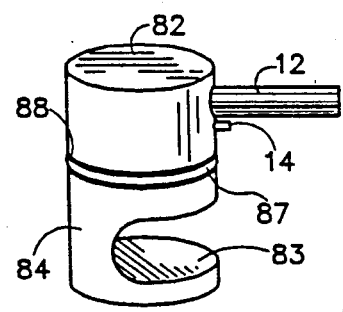
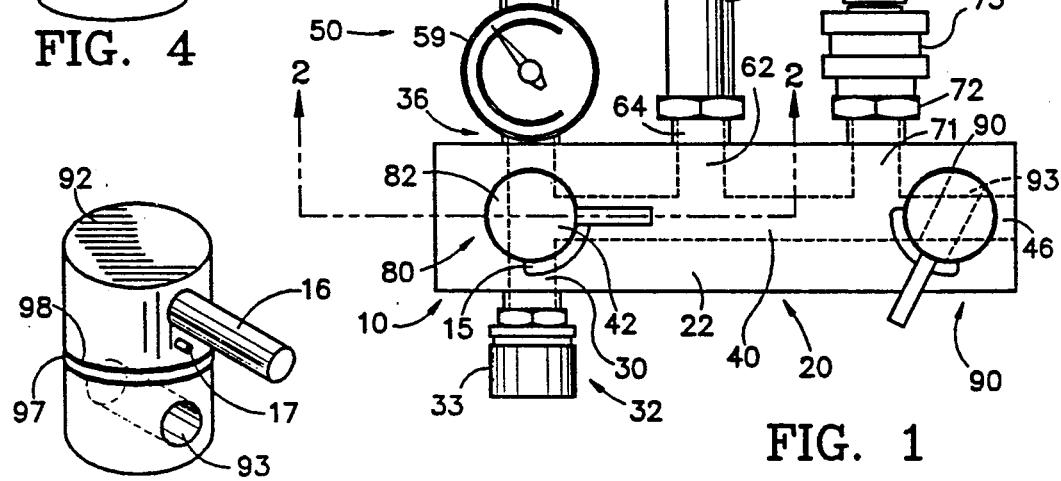

COMPRESSED GAS SAMPLING DEVICE

BACKGROUND OF THE INVENTION

1. Field of the Invention

This invention relates in general to a compressed gas sampling device and more specifically involves a manifold and valving device for taking plenum and filter samples from a wide variety of compressed gas sources under actual working conditions.

2. Description of the Related Art

Gas from compressed gas sources is sampled periodically to determine its composition and purity. Periodic sampling is particularly important where the compressed gas is to be used for human respiration, such as in scuba diving. Compressed gas may contain solid contaminants such as dirt, grime, or metal filings which can foul or completely jam a regulator or solid contaminants such as oil mist which can damage a person's lungs and also cause anoxia and death. Gaseous contaminants, such as carbon monoxide, may also cause anoxia, death or severe lung or nerve damage.

Typically, gas compressor output is sampled in the field by non-technical personnel using a field kit. The typical sampling of a gas compressor includes obtaining a plenum sample, i.e. a sample of the compressed gas output in a sampling bomb, and obtaining a filter sample, i.e. passing a known volume of the compressed gas output thru a filter device including a filter so that solid contaminants are trapped in the filter. The filter sample and the plenum sample are commonly sent to a laboratory where the filter is examined for solid contaminants and the plenum is analysed, such as by gas chromatography.

A wide variety of compressors are in use and they vary greatly in their capacity, i.e. in the volume of gas output and in the pressure of that volume. For example, typical low volume/high pressure compressors, such as for diving, output 10-20 SCFM at 3,000 PSI. Small compressors may output a very small volume, for example 3 SCFM or less. A typical large volume/low pressure compressor produces 60-200 SCFM at 225 PSI.

There are a number of disadvantages in conventional compressed gas sampling devices.

Because conventional sampling devices only operate effectively over a small pressure and volume range, a wide variety of sampling devices are in use corresponding to the wide variety of compressor outputs. Therefore, it is desirable to have a single sampling device that can be used for a wide variety of compressors.

Some conventional sampling devices control the pressure to the device by use of a regulator or other throttling device or critical orifices placed in the gas stream before the sampling device. Such devices present impinging surfaces, thereby trapping solid contaminants such that they do not reach the filter. Therefore, it is desirable to have a sampling device that has no front regulator or throttling device so that solid contaminants reach the analytical filter.

The amount of carbon monoxide and film mist in compressor output may be largely dependent on how hard the compressor is working. Many conventional sampling devices do not sample a compressor under actual working conditions. Therefore, it is desirable to have a sampling device that samples the gas output of a compressor under actual working conditions.

SUMMARY OF THE INVENTION

The invention is a sampling device for sampling the output of compressed gas sources, such as air compressors, for solid contaminants, such as debris and oil mist, and for gaseous contaminants, such as carbon monoxide. The sampling device generally comprises a manifold including a first conduit and a second conduit, a filter device, safety valve, a sampling bomb, a flow director valve, and a pressure control valve.

The first conduit has a receiving end for receiving compressed gas from a compressed gas source and an exit end connected to a filter sampling device. The second conduit has an inlet end connected to the first conduit between its receiving and exit ends and has a vent end.

A flow director valve at the junction of the first and second conduits is operable from a full shunt position wherein all incoming gas is directed into the second conduit and a full open position wherein incoming gas is directed to the exit end or the second conduit.

A pressure control valve disposed in the second conduit near the vent end is adjustable to operable at all positions at and between a full venting position wherein gas in the second conduit is directed out of the vent end and a fully closed position wherein no gas in the second conduit may pass out of vent end.

A sampling bomb is connected to the second conduit between the inlet end and the pressure control valve. A pressure relief valve may also be so connected.

This sampling device enables a user to sample with a single device compressors of widely varying pressure and volume outputs while the compressor is operating at its maximum output.

BRIEF DESCRIPTION OF THE DRAWING

FIG. 1 is a top view of a preferred embodiment of the compressed gas sampling device of the current invention.

FIG. 2 is a sectional view of the flow director valve portion of the device taken on line 2—2 of FIG. 1.

FIG. 3 is a sectional view of the flow director valve and first and second conduits taken on line 3—3 of FIG. 2.

FIG. 4 is a frontal elevated perspective view of the flow director valve of FIG. 3.

FIG. 5 is a perspective view of the pressure control valve of FIG. 1.

DETAILED DESCRIPTION OF THE INVENTION

With reference now to the drawing, there is shown in FIG. 1 a top view of a preferred embodiment of the gas sampling device, denoted generally as 10, of the current invention. Sampling device 10 generally comprises a manifold, denoted generally as 20, a filter device means, denoted generally as 50, a safety valve means, denoted generally as 60, a sampling bomb means, denoted generally as 70, a flow director valve means, denoted generally as 80, and pressure control valve means, denoted generally as 90.

Manifold 20 includes a body 22 containing conduits, shown in phantom, for transport of compressed gas. Body 22 may be constructed of suitably strong, relatively inert material, such as aluminum or stainless steel.

First conduit 30 passes through body 22 and includes a receiving end 32 for receiving a flow of compressed gas and an exit end 36. Receiving end 32 includes means, such as common quick release fitting 33, for attachment of a compressed gas source. In the preferred embodiment, first conduit 30 is 0.375 inches in diameter.

Second conduit 40 passes through body 22 and includes an inlet end 42 connected to first conduit 30 between receiving end 32 and exit end 36 for receiving compressed gas from the first conduit and a vent end 46 for venting gas, such as to the atmosphere. In the preferred embodiment shown, second conduit 40 is 0.375 inches in diameter.

Filter device means 50 is attached to exit end 36 for receiving compressed gas therefrom, for passing the received gas through a filter 51, shown in phantom, in filter housing 52, and for expelling the filtered gas, such as to the atmosphere through expelling port 58, shown in phantom. Filter housing 52 generally comprises attachment portion 54 for attachment to exit end 36 and removable cap 56. Cap 56 is attached to attachment portion 54 such as by screw threads and is disengaged to remove and replace the filter.

Filter device 50 includes means, such as pressure gauge 59, in fluid communication with gas passing through the filter for indicating the gas flow volume through the filter. Gas flow rate is a function of the pressure reading on pressure gauge 59. In the preferred embodiment shown, the expelling hole is 5/32 inches in diameter.

Safety valve means 60, includes relief valve 66, relief port 64, and relief conduit 62. Relief valve 66, connected to relief port 64 and in fluid communication with second conduit 40 via relief conduit 62, opens to vent air from second conduit 40 to the atmosphere when the pressure in second conduit 40 is above a predetermined level. Such safety relief valves 66 are well known in the art and are not described in detail here. A typical safety relief valve 66 opens at 60 PSI and vents 100 SCFM. Relief conduit 62 is attached to second conduit 40 between input end 42 and pressure control valve means 90.

Sampling bomb means 70 includes sampling conduit 71, sampling port 72, fastener, such as quick release fastener 73, first valve means, such as one way check valve 74, bomb pressure gauge 75, pressure vessel 76, and second valve means, such as bomb valve 78.

Pressure vessel 76 includes a chamber for storing a volume of compressed gas received from second conduit 40 via sampling conduit 71, sampling port 72, fastener 73, and valve 74. Check valve 74 allows gas from second conduit 40 to pass into vessel 76 but not return. Depending on the application, first valve means may be a fully operable open/close valve similar to valve 78. Pressure bomb gauge 75 indicates the pressure of the gas sample in pressure vessel 76. Bomb valve 78 may be initially opened so that incoming gas to be stored expels any residual gas out bomb port 79. Bomb valve 78 is closed to store a gas sample. Release fitting 73 and check valve 74 allow separation of pressure vessel 76 from manifold 20 so that pressure vessel may be sent to the lab for analysis.

Flow director valve means 80 is disposed in first conduit 30 and is operable between a full shunt position, wherein fluid communication between receiving end 32 and exit end 36 is blocked and wherein fluid communication between receiving end 32 and inlet end 42 is provided, and a full open position, wherein fluid communication is provided between receiving end 32 and exit end 36 and inlet end 42.

Referring now also to FIGS. 2, 3, and 4, in the preferred embodiment shown, flow director valve means 80 includes blind cylindrical bore 81 into manifold body 22 at the junction of first conduit 30 and second conduit 40. Cylindrical director valve 82 is disposed in and rotatable in bore 81. Director valve 82 includes a channel 83 cut into one side such that in the open position, as shown in FIGS. 1, 2, and 3, gas from receiving end 32 may pass unimpeded to exit end 36 and such that received gas is also in communication with second conduit 40. As best seen in FIG. 2, rotation of director valve 82 ninety degrees clockwise positions it in the closed position, wherein the non-channel portion 84 of director valve 82 blocks gas flow to exit end 36 while still allowing gas flow to second conduit 40.

Director valve 82 is retained in manifold body 22 with means such as screw through a bore in body 22 and terminating in a threaded blind bore in director valve 82. Director valve sealing means, such as top O-ring 87 in annular groove 88 and bottom O-ring 85 in circular groove 86, prevent escape of compressed gas from the device 10. Handle 12 provides means for manually turning and thus operating director valve 82. A set pin 14 protruding from director valve 82 and terminating in ninety degree groove 15 in body 22 provides definitive end stops so that director valve 82 can be manipulated between full open and full shunt rapidly and positively.

Referring now to FIGS. 1 and 5, in the preferred embodiment shown, pressure control valve means 90 includes cylindrical control valve 91 mounted into into a blind bore in manifold body 22 in a similar manner to that of flow director valve 82. Except as noted, control valve 93 is mounted and sealed similar to that of director valve 80. Control valve blind bore bifurcates second conduit 40 near vent end 46. Control valve 82 is disposed in and rotatable in the bore. Control valve 93 is rotatable from a full open position whereby passageway 93 therethrough is aligned with second conduit 40 for passage of compressed gas from second conduit 40 out vent end 46 to a fully closed position whereby no gas may pass through passageway 93. Similar to director valve 82, associated with control valve 92 is handle 16, set pin 17, O-ring 97 in circular groove 88, and body groove 18.

The compressed gas sampling device 10 allows sampling of compressors at full flow because excess gas can always be vented off. Flow director valve 82 assures that received gas can pass toward pressure control valve 93 at all times. With flow director valve 82 in the full shunt position, by manipulating the pressure control valve 92, the operator controls the amount of gas vented and thereby controls the pressure inside of second conduit 40 and thereby the pressure to sampling bomb means 70. With flow director valve 82 in the full open position, by manipulating pressure control valve 92 the operator controls the pressure in manifold body 22 including first conduit 30 and second conduit 40; thereby controlling the flow rate through filter expelling hole 58.

The compress gas sampling device 10 of the present invention enables sampling by a single device of compressors having vastly different flow rates. For example, the sampling device 10 as shown an described can sample compressors with flow rates in the range of 3-250 SCFM and do so while the compressor is operating at its maximum output. This covers almost all of the compressors being used today. Slight modifications in the dimensions will modify this range. Importantly, with the sampling device 10 of the present invention, one can have high confidence of being able to sample any compressor even without knowledge of the compressor's pressure or flow rate.

From the foregoing description, it is seen that the present invention provides an extremely simple, efficient, universal, and reliable manner sampling compressed gas sources.

Although a particular embodiment of the invention has been illustrated and described, various changes may be made in the form, construction, and arrangement of the parts without sacrificing any of its advantages, and it is to be understood that all matter herein is to be interpreted as illustrative and not in any limiting sense and that it is intended to cover in the appended claims such modifications and changes as come within the true spirit and scope of the invention.

I claim:
1. A compressed gas sampling device comprising:
 a first conduit comprising:
  a receiving end for receiving a flow of compressed gas to be sampled; and
  an exit end;
 filter device means including:
  a filter; and
  flow indicator means for indicating the gas flow volume thru said filter;
 said filter device means attached to said exit end for receiving compressed gas from said exit end, for passing the received compressed gas through said filter, and for expelling the filtered gas;
 a second conduit comprising:
  an inlet end connected to said first conduit between said receiving end and said exit end; and
  a vent end;
 flow director valve means disposed in said first conduit and operable between a full shunt position, wherein fluid communication between said receiving end and said exit end is blocked and wherein fluid communication between said receiving end and said inlet end is provided, and a full open position wherein fluid communication is provided between said receiving end and said exit end and said inlet end; and
 pressure control valve means disposed in said second conduit for controlling gas flow out of said vent end.

2. The compressed gas sampling device of claim 1 wherein said flow indicator means is a pressure guage.

3. The compressed gas sampling device of claim 1 further comprising:
 safety valve means connected to said second conduit between said inlet end and said pressure control valve for releasing compressed gas from said second conduit when the gas pressure in said second conduit is above a predetermined level.

4. The compressed gas sampling device of claim 1 further comprising:
 sampling bomb means including a chamber; said sampling bomb means connected to said second conduit between said inlet end and said pressure control valve for receiving compressed gas from said second conduit and for storing the received compressed gas in said chamber.

5. The compressed gas sampling device of claim 4 wherein said sampling bomb means further includes:
 pressure gauge means for indication the pressure in said chamber.

6. The compressed gas sampling device of claim 4 wherein said sampling bomb means further includes:
 first valve means connected to said chamber and to said second conduit for receiving compressed gas from said second conduit, for allowing received gas to flow into said chamber, and for retaining gas in said chamber.

7. The compressed gas sampling device of claim 6 wherein: said first valve means is a one-way valve.

8. The compressed gas sampling device of claim 4 wherein said sampling bomb means further includes:
 second valve means connected to said chamber for allowing gas to exit said chamber.

9. The compressed gas sampling device of claim 1 wherein: said flow director valve, in the full open, does not impede the movement of compressed gas from said receiving end to said exit end.

10. The compressed gas sampling device of claim 1 wherein: said flow director valve, in the full open position, does not impede the movement of compressed gas from said receiving end to said exit end; and said first conduit and said filter device means are so configured that, when said flow director valve is in the full open position, received compressed gas may pass in substantially a straight line from said receiving end to said filter.

11. A compressed gas sampling device comprising:
 a first conduit comprising:
  a receiving end for receiving a flow of compressed gas to be sampled; and
  an exit end;
 filter device means including:
  a filter; and
  flow indicator means for indicating the gas flow volume through said filter device means; said filter device means attached to said exit end for receiving compressed gas from said exit end, for passing the received compressed gas through said filter, and for expelling the filtered gas;
 a second conduit comprising:
  an inlet end connected to said first conduit between said receiving end and said exit end; and
  a vent end;
 flow director valve means disposed in said first conduit and operable between a full shunt position that blocks fluid communication between said receiving end and said exit end and provides fluid communication between said receiving end and said inlet end, and a full open position that provides fluid communication between said receiving end and said exit end and said inlet end;
 pressure control valve means disposed in said second conduit for controlling gas flow out of said vent end; and
 sampling bomb means including a chamber; said sampling bomb means connected to said second conduit between said inlet end and said pressure control valve for receiving compressed gas from said second conduit and for storing the received compressed gas in said chamber.

12. The compressed gas sampling device of claim 11 wherein:
 said flow director valve, in the full open, does not impede the movement of compressed gas from said receiving end to said exit end.

13. The compressed gas sampling device of claim 11 wherein:

said flow director valve, in the full open position, does not impede the movement of compressed gas from said receiving end to said exit end; and said first conduit and said filter device means are so configured that, when said flow director valve is in the full open position, received compressed gas may pass in substantially a straight line from said receiving end to said filter.

14. The compressed gas sampling device of claim 11 wherein said sampling bomb means further includes:
first valve means connected to said chamber and to said second conduit for receiving compressed gas from said second conduit, for allowing flow of received gas into said chamber, and for retaining gas in said chamber.

15. The compressed gas sampling device of claim 14 wherein:
said first valve means is a one-way valve.

16. The compressed gas sampling device of claim 14 wherein said sampling bomb means further includes:
second valve means connected to said chamber for allowing gas to exit said chamber.

17. The compressed gas sampling device of claim 16 wherein:
said flow director valve, in the full open, does not impede the movement of compressed gas from said receiving end to said exit end.

18. The compressed gas sampling device of claim 16 wherein:
said flow director valve, in the full open position, does not impede the movement of compressed gas from said receiving end to said exit end; and said first conduit and said filter device means are so configured that, when said flow director valve is in the full open position, received compressed gas may pass in substantially a straight line from said receiving end to said filter.

* * * * *